(12) United States Patent
Searcey et al.

(10) Patent No.: US 7,179,921 B2
(45) Date of Patent: Feb. 20, 2007

(54) INDOLINE AND TETRAHYDRO-QUINOLINES AS PRODRUGS FOR TUMOUR TREATMENT

(75) Inventors: Mark Searcey, London (GB); Laurence Hylton Patterson, London (GB)

(73) Assignee: School of Pharmacy, University of London, London (GB)

( * ) Notice: Subject to any disclaimer, the term of this patent is extended or adjusted under 35 U.S.C. 154(b) by 0 days.

(21) Appl. No.: 10/468,743

(22) PCT Filed: Feb. 22, 2002

(86) PCT No.: PCT/GB02/00785

§ 371 (c)(1), (2), (4) Date: Mar. 29, 2004

(87) PCT Pub. No.: WO02/067937

PCT Pub. Date: Sep. 6, 2002

(65) Prior Publication Data

US 2004/0157880 A1 Aug. 12, 2004

(30) Foreign Application Priority Data

Feb. 22, 2001 (EP) .................................. 01301609

(51) Int. Cl.
  C07D 215/02 (2006.01)
  C07D 209/04 (2006.01)
(52) U.S. Cl. ...................... 546/165; 514/412; 514/311; 548/491; 548/490
(58) Field of Classification Search ................ 514/311, 514/412; 546/165; 548/491, 490
See application file for complete search history.

(56) References Cited

FOREIGN PATENT DOCUMENTS

| EP | 0 461 603 | 12/1991 |
|---|---|---|
| EP | 0 702 004 | 3/1996 |
| JP | 08143565 | * 6/1996 |

OTHER PUBLICATIONS

Tietz, Bioorganic & Medicinal Chemistry vol. 9, pp. 1929-1939, 2001.*
Rahuel, Chemistry & Biology, vol. 7(7), pp. 493-504, 2000.*
Biniecki, CA 110:231404, abstract of Acta poloniae Pharmaceutica, 1988, 45(1), pp. 14-17.*
Boger et al., Journal of the American Chemical Society, vol. 112, pp. 8961-8970 (1990).
Boger et al., Journal of Organic Chemistry, vol. 62, pp. 8875-8891 (1997).
Boger et al., Journal of the American Chemical Society, vol. 116, pp. 11335-11348 (1994).
Atwell et al., Bioorganic & Medicinal Chemistry Letters, Oxford, GB, vol. 7, pp. 1493-1496 (1997).

* cited by examiner

*Primary Examiner*—D. Margaret Seaman
(74) *Attorney, Agent, or Firm*—Dickstein Shapiro LLP

(57) ABSTRACT

Compounds of the general formula I or IA or a salt in which X is H, Y is a leaving group, $R^1$ preferably being an aromatic DNA binding subunit are prodrug analogues of duocarmycin. The compounds are expected to be hydroxylated at the carbon atom to which X is joined, by cytochrome P450, in particular by CYP1B1, expressed at high levels in tumours. The prodrug is expected to be activated preferentially in tumour cells, where it will act as a DNA alkylating agent preventing cell division

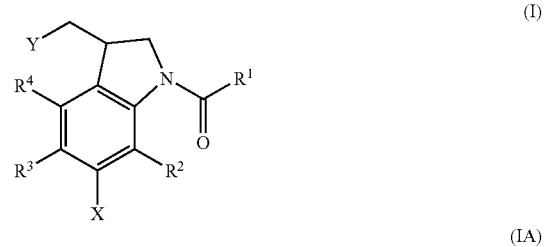

(I)

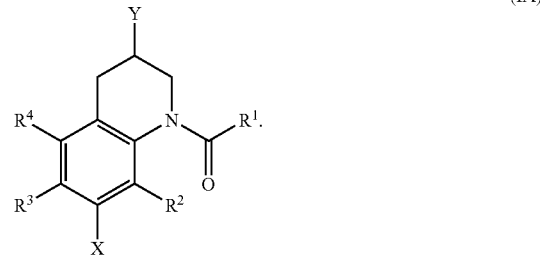

(IA)

8 Claims, No Drawings

INDOLINE AND TETRAHYDRO-QUINOLINES AS PRODRUGS FOR TUMOUR TREATMENT

The present invention concerns aromatic oxidation/hydroxylation activated prodrugs, particularly anti-tumour prodrugs and those which are specifically activated by the oxidation/hydroxylation activities of the cytochrome P450 family of enzymes.

Many conventional cytotoxic drugs are known that can be used for therapeutic purposes. However, they typically suffer from the problem that they are generally cytotoxic and therefore may affect cells other than those that are required to be destroyed. This can be alleviated to some extent by the use of targeted drug delivery systems, for example direct injection to a site of tumourous tissue or, e.g. binding the cytotoxic agent to an antibody that specifically recognises an antigen displayed only on the cancer cell surface. Alternatively, electromagnetic radiation may be used to cause chemical alteration in an agent at a desired site such that it becomes is cytotoxic. However, all of these techniques have, to a greater or lesser extent, certain limitations and disadvantages.

The compound (+)-CC-1065 and the duocarmycins are naturally occurring representatives of a class of DNA alkylating agents. The naturally occurring compounds consist of a DNA alkylating unit based upon a pyrrolo[3,2-e]indole core, with one or two sub units, conferring DNA binding capabilities. CC-1065 and duocarmycin A comprise a spirocyclic cyclopropane group responsible for the DNA alkylation properties. Duocarmycin $B_2$, $C_2$ and $D_2$ are believed to be precursors for cyclopropane actives, and comprise a substituted (by a leaving group) methyl group at the eight position on the dihydro pyrrole ring. CC-1065 has been synthesised by various routes, summarised by Boger et al in Chem. Rev. 1997, 97, 787–828.

In U.S. Pat. No. 4,413,132 the first synthesis of the left hand sub-unit of CC-1065 was described. The synthesis is based on a Winstein Ar-3' alkylation in which the cyclopropane ring is introduced. In a previous step, the A ring (of the indole core) is introduced by reaction of an aniline with an α-thiomethylester using chemistry based on Gassman's Oxindole Synthesis. The aniline has a protected phenolic hydroxyl group ortho to the $NH_2$ group, which, in the final product, is believed to be crucial for DNA alkylation. CC-1065 has broad antitumour activity but is too toxic against normal cells to be clinically useful.

Attempts have been made to target the delivery of CC-1065 and analogues by conjugating the drug via the DNA binding subunit to polymers, or specific binding agents such as antibodies or biotin described in U.S. Pat. No. 5,843,937. Boger et al in Synthesis 1999 SI, 1505–1509 described prodrugs of 1,2,9,9a-tetrahydrocyclopropa(c)benz[e]indol-4-one, in which the cyclopropane ring-opened version of the compounds were derivatised by reaction of the phenolic group to form esters and carbamates.

In Tet. Letts. (1998) 39, 2227–2230 Boger et al describe the synthesis of some CC-1065 analogues including the compound

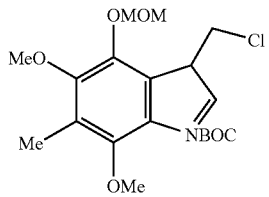

in which OMOM is an alkoxy alkoxy group. The compound is proposed as a precursor of a mitomycin hybrid, ie the cyclopropane-ring-closed indoline form.

In J.Am.Chem.Soc. (1991), 113, 3980-'83 Boger et al describe a study to identify features of CC-1065 analogues contributing to the selectivity of the DNA-alkylation. The compounds tested in vitro had alkylating subunits based on 2,3-dihydroindole and included the 6-deshydroxy analogues. These were shown to have some DNA alkylating properties though at concentrations $10^4$ times higher than that of the 6-hydroxy compounds.

The present invention relates to precursors of analogues of CC-1065 which are indole derivatives, which do not have the hydroxyl group in the benzene ring of indole alkylating sub unit, and which are hence substantially inactive as DNA alkylating agents themselves.

It has been reported (Murray, G. I. et al., 15 Jul. 1997, Cancer Research, 57m 3026–3031 and WO-A-9712246) that the enzyme CYP1B1, a member of the cytochrome P450 (CYP) family of xenobiotic metabolising enzymes, is expressed at a high frequency in a range of human cancers, including cancers of the breast, colon, lung, oesophagus, skin, lymph node, brain and testes, and that it is not detectable in normal tissues. This led to the conclusion that the expression of cytochrome P450 isoforms in tumour cells provides a molecular target for the development of new antitumour drugs that could be selectively activated by the CYP enzymes in tumour cells, although no drug examples were given. A number of other CYP isoforms have been shown to be over expressed in various tumours.

Many of the CYP's expressed in tumours are mentioned in Patterson, L H et al, (1999) Anticancer Drug Des. 14(6), 473–486.

In WO-A-99/40056 prodrugs of styrene- and chalcone-derivatives are described. The respective hydroxylated forms of the prodrugs, formed in situ, are potent tyrosine kinase (TK) inhibitors. Inhibition of TK activity contributes to tumour inhibition and cell destruction. The prodrugs were shown to be activated by microsomal preparations expressing CYP1B1 enzyme, and to have cytotoxic activity against cell lines expressing the same enzyme, whilst having much lower cytotoxic activity against cell lines not expressing the enzyme.

The present invention is directed to a new class of prodrugs which are expected to be hydroxylated in situ by CYP enzymes, in particular enzymes expressed at high levels in tumours as described by Patterson L H, et al, op. cit .. In particular the prodrugs are believed to be metabolisable by CYP1 B1 enzyme. Some of the compounds are new. The present invention relates to the first therapeutic use of a broad range of compounds.

There is provided according to the first aspect of the invention the new use of a compound of the general formula I or IA or a salt thereof in the manufacture of a composition for use in a method of treatment by therapy of an animal:

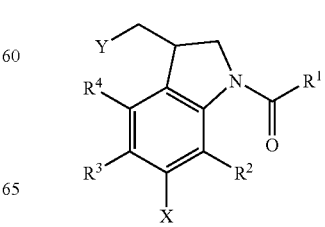

-continued

IA

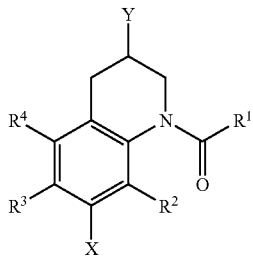

in which X is H;

Y is a leaving group; (preferably selected from OCOOR$^5$, OCONHR$^6$, Cl, Br, I and OSO$_2$R$^7$ in which R$^5$, R$^6$, and R$^7$ are each selected from C$_{1-4}$ alkyl, optionally substituted phenyl, C$_{1-12}$ aralkyl and optionally substituted heteroaryl);

R$^1$ is —Ar, NH$_2$, R$^8$ or OR$^8$;

R$^2$ and R$^3$ are each independently selected from H, C$_{1-4}$ alkyl, —OH, C$_{1-4}$ alkoxy, —CN, Cl, Br, I, —NO$_2$, —NH$_2$, —NHCOR$^9$, —COOH, —CONHR$^{10}$, —NHCOOR$^{10}$ and —COOR$^{10}$;

R$^4$ is selected from H, C$_{1-4}$ alkyl, CN, Cl, Br, I, NO$_2$, NH$_2$, —NHCOR$^9$, —COOH, —CONHR$^{10}$, —NHCOOR$^{10}$ and —COOR$^{10}$;

R$^8$, R$^9$ and R$^{10}$ are independently selected from C$_{1-4}$ alkyl, optionally substituted phenyl, C$_{7-12}$-aralkyl and optionally substituted heteroaryl and ligands;

Ar is selected from

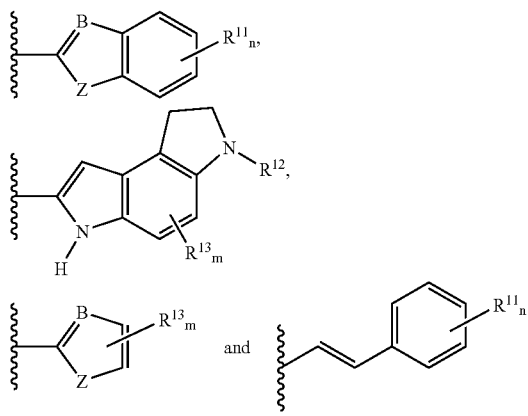

in which B is N or CR$^{14}$;

Z is O, S —CH═CH— or NH;

the or each R$^{11}$ is selected from OH, C$_{1-4}$ alkoxy, C$_{1-4}$ alkyl, —NO$_2$, —NH$_2$, —NHR$^{17}$, —NR$^{17}{}_2$, —N$^+$R$^{17}{}_3$, —CN, Cl, Br, I, —NHCOR$^{15}$, —COOH, —CONHR$^{16}$, —NHCOOR$^{16}$ and COOR$^{16}$;

n is an integer in the range 0 to 4;

R$^{12}$ is H, —COAr$^1$, —CONH$_2$, —COOH, —COR$^{16}$ or —COOR$^{16}$;

the or each R$^{13}$ is selected from OH, C$_{1-4}$ alkoxy, C$_{1-4}$ alkyl, —NO$_2$, —NH$_2$, —NHR$^{17}$, —NR$^{17}{}_2$, —N$^+$R$^{17}{}_3$, —CN, Cl, Br, I, —NHCOR$^{15}$, —COOH, —CONHR$^{16}$, —NHCOOR$^{16}$ and —COOR$^{16}$;

m is 0, 1 or 2;

R$^{14}$ is selected from OH, C$_{1-4}$ alkoxy, C$_{1-4}$ alkyl, —NO$_2$, —NH$_2$, —CN, Cl, Br, I, —NHCOR$^{15}$, —COOH, —CONHR$^{16}$, —COOR$^{16}$, —NHCOOR$^{16}$ and H;

R$^{15}$ is selected from C$_{1-4}$ alkyl, optionally substituted phenyl, optionally substituted heteroaryl, C$_{7-12}$ aralkyl, a ligand and Ar$^1$;

R$^{16}$ is selected from C$_{1-4}$ alkyl, optionally substituted phenyl, C$_{7-12}$-aralkyl and optionally substituted heteroaryl and a ligand;

each R$^{17}$ is selected from C$_{1-4}$ alkyl, optionally substituted phenyl, optionally substituted heteroaryl and C$_{7-12}$-aralkyl; and Ar$^1$ is selected from the same groups as Ar, provided that no more than one group R$^{11}$ or R$^{13}$ in any one ring includes a group Ar$^1$.

The animal which is treated is generally a human, although the compounds may also have veternary use. The indication treated is generally cancer including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The tumour may, for instance, be defined as a tumour expressing high levels of CYP1B1.

In the invention, the leaving group Y is, for instance, a leaving group which has utility in nucleophilic substitution reactions. Suitable examples of such groups are —OCOOR$^5$, —OCONHR$^6$, Cl, Br, I, or —OSOOR$^7$, in which R$^5$, R$^6$ and R$^7$ are each selected from C$_{1-4}$ alkyl, optionally substituted phenyl, C$_{7-12}$-aralkyl and optionally substituted heteroaryl. Most preferably the leaving group is a halogen atom, preferably chlorine.

Optional substituents in phenyl, aralkyl and heteroaryl groups are, for instance, C$_{1-4}$-alkyl, halogen, hydroxyl, C$_{1-4}$-alkoxy, —NH$_2$, —NHR$^{17}$—, —NR$^{17}{}_2$, —N$^+$R$^{17}{}_3$, —NO$_2$—, —CN, —COOH, —NHCOR$^{15}$, —CONHR$^{16}$, —NHCOOR$^{16}$, —COOR$^{16}$ etc.

In the present invention the term ligand includes a group having specific targeting characteristics, useful for instance in antibody or gene-directed enzyme prodrug-type environments. A ligand may be an oligopeptide, biotin, avidin or streptavidin, a polymeric group, an oligonucleotide or a protein. Preferably it has specific binding characteristics such as an antibody or fragment, an antigen, a sense or anti-sense oligo-nucleotide, or one of avidin, streptavidin and biotin, that is it is one component of a specific binding pair. Alternatively it may be a group designed for passive targeting, such as a polymeric group, or a group designed to prolong the stability or reduce immunogenicity such as a hydrophilic group. U.S. Pat No. 5,843,937 discloses suitable ligands for conjugating to these types of actives and methods for carrying out the conjugation.

The group Ar$^1$ is preferably

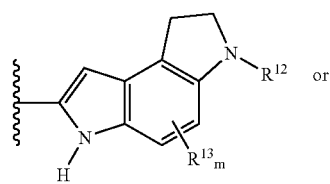

-continued

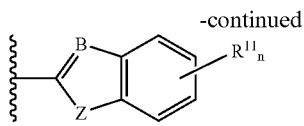

Preferably $R^1$ is other than —$OR^8$ in a pharmaceutically active compound. In general, for optimised DNA binding ability, the group $R^1$ in a compound of the general formula I or IA is a group Ar. Often the compound may include two aromatic groups joined to one another. In such compounds, one of the groups $R^{11}$ of the Ar group, or the group $R^{12}$, as the case may be, is a group $Ar^1$. Whilst for some compounds it may be desirable for three or more such aromatic groups to be linked, it is preferred that there is one group Ar and one group $Ar^1$. Thus in a group $Ar^1$ which is a pyrrolo-dihydroindole type of group, the group $R^{12}$ should be other than a group $COAr^1$. In a group $Ar^1$ which is one of the other types of groups there should either be no substituents $R^{11}$ or $R^{13}$, as the case may be, or, if there are any substituents, no such substituent should include a group $Ar^1$.

According to one embodiment of the invention, the substituent Ar is a group

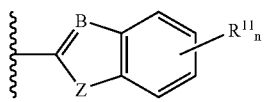

In such groups Ar, B is preferably $CR^{14}$. $R^{14}$ is preferably H. The definition of Z is preferably NH, although furan (Z=O) and thiophene (Z=S) analogues had been generated for conjugation to DNA alkylating units and may have useful DNA binding characteristics. Similarly, in a group $Ar^1$, the groups B and Z are selected amongst the same preferable groups. Preferably n is at least 1 and one of the groups $R^{11}$ is —$NHCOAr^1$. In this embodiment $Ar^1$ is preferably a group

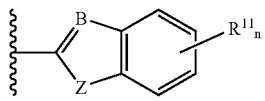

in which B and Z are the same as in Ar.

In another embodiment the substituent Ar is a group

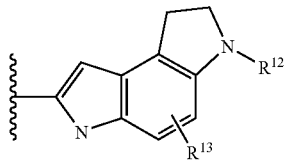

Preferably $R^{12}$ in such a group Ar is other than $COOR^{16}$, more preferably it is a group —$COAr^1$, in which $Ar^1$ preferably is the same type of group.

In both groups Ar and $Ar^1$, m in the indole type group is preferably zero.

In Ar and $Ar^1$, there may be several substituents $R^{11}$. Most preferably such substituents are selected amongst $C_{1-4}$-alkoxy groups.

In compounds of the formula I, the core benzene ring of the DNA alkylating sub-unit is preferably unsubstituted ($R^3$ and $R^4$ are both hydrogen).

In the compounds of the formula I, X is H. It is believed that, hydroxylation of the compound will occur in situ at the carbon atom to which X is attached, thereby activating the compound enabling it to act as a DNA alkylating agent.

The present invention further provides pharmaceutical compositions comprising compounds of the formula I and IA or salts and a pharmaceutically acceptable excipient. Pharmaceutical compositions may be suitable for intramuscular, intraperitoneal, intrapulmonary, oral or, most preferably, intravenous administration. The compositions contain suitable matrixes, for example for controlled or delayed release. The compositions may be in the form of solutions, solids, for instance powders, tablets or implants, and may comprise the compound of the formula I in solid or dissolved form. The compound may be incorporated in a particulate drug delivery system, for instance in a liquid formulation. Specific examples of suitable excipients include lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate. Solid compositions may take the form of powders and gels but are more conveniently of a formed type, for example as tablets, cachets or capsules (including spansules). Alternative, more specialised types of formulation including liposomes, nanosomes and nanoparticles.

It is believed that compounds of the general formula IA may be novel compounds.

One compound of the general formula I (in which $R^1$ is —O—tBu, $R^2$, $R^3$ and $R^4$ are all H, and Y is $OSO_2CH_3$) was synthesised by Boger et al, J.Am. Chem. Soc (1991) 113, 3980–5983. Others may be made by analogous techniques. It is convenient to form the DNA alkylating sub unit in one series of steps and to attach this through the nitrogen atom of the dihydro-pyrrole or tetrahydroquinoline was as the case may be, ring to the rest of the molecule. The DNA alkylating sub-unit may be conjugated to DNA binding sub-units synthesised as described in Boger et al, 1997 op. cit., for instance the PDE-I and PDE-II sub-units described in that reference.

The compounds of the formula I and IA may be synthesised in a method in which a compound of the formula II or IIA, as the case may be,

II

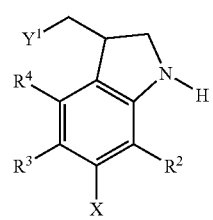

-continued

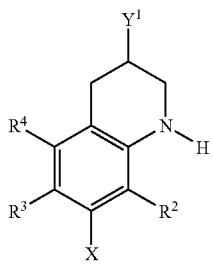
IIA in which X, R², R³ and R⁴ are as defined above; and
Y¹ is a leaving group or is hydroxyl; is reacted with a compound of the general formula III $$R^{18}COY^2 \qquad III$$

in which R¹⁸ is selected from $C_{1-4}$-alkyl, optionally substituted phenyl, $C_{7-12}$-aralkyl, optionally substituted heteroaryl and Ar²;
Ar² is selected from

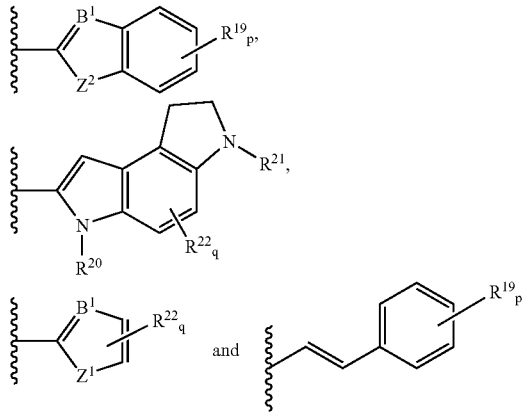

in which B¹ is N or CR²³;
Z¹ is O, S, —CH=CH— or NR²⁴;
the or each R¹⁹ is selected from $C_{1-4}$-alkoxy, $C_{1-4}$-alkyl, NO₂, CN, Cl, Br, I, —NHR²⁴, —NR²⁵₂, —N⁺R²⁵₃—, I, —NHCOR²⁶, —COOH, —CONHR²⁷ and —COOR²⁷;
p is an integer in the range 0 to 4;
R²⁰ is an amine protecting group;
R²¹ is an amine protecting group, —CONH₂, —COOH, —COR²⁷ or —COAr³;
the or each R²⁰ is selected from $C_{1-4}$-alkoxy, $C_{1-4}$-alkyl, NO₂, CN, Cl, Br, I, —NHR²⁴, —NR²⁵₂, —N⁺R²⁵₃—, NHCOR²⁶, —COOH, —CONHR²⁷ and —COOR²⁷;
q is 0, 1 or 2;
R²³ is selected from H, $C_{1-4}$-alkoxy, $C_{1-4}$-alkyl, NO₂, CN, Cl, Br, I, —NHR²⁴, —NR²⁵₂, —N⁺R²⁵₃—, NHCOR²⁶, COOH, —CONHR²⁷ and COOR²⁷;
R²⁴ is an amine protecting group;
R²⁶ is selected from Ar³, $C_{1-4}$-alkyl, optionally substituted phenyl, $C_{7-12}$-aralkyl, optionally substituted heteroaryl and a ligand;
each R²⁵ is selected from H, $C_{1-4}$-alkyl, optionally substituted phenyl, $C_{7-12}$-aralkyl and optionally substituted heteroaryl;
R²⁶ is selected from $C_{1-4}$-alkyl, optionally substituted phenyl, $C_{7-12}$-aralkyl optionally substituted heteroaryl and a ligand;
Ar³ is selected from the same groups as Ar²; and Y² is a leaving group, provided that no more than one R¹⁹ or R²² in any one ring includes a group Ar³.
Preferably a group Ar³ is

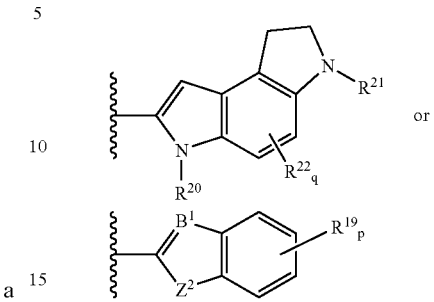

Y² is, for instance, selected amongst the preferred leaving groups listed above for Y. Most suitably the definition of Y² is Cl. Alternatively, the group Y² may be OH. In this case, it may be necessary to include a coupling agent to assist in the coupling reaction.

Y¹ may be the same as Y or may be another leaving group, or hydroxyl, which may be converted to Y in a subsequent step.

The reaction between the compound of the general formula II or A, as the case may be, and the carboxylic acid or derivative of the general formula II is carried out under conditions allowing such coupling to take place. Such conditions are similar to those generally used for formation of peptide bonds, for instance as used in peptide synthetic methods.

After the coupling process, it may be desirable to deprotect one or more of any protected amine groups. If further reaction, for instance with other derivatising agents such as glycosyl compounds, peptides, polymers etc is desired through any such amine groups, it may be desirable to deprotect only those to which subsequent reaction to to take place, whilst retaining the other amine groups in a protected form. Selection of suitable amine protecting groups and protection and deprotection protocols may be made using techniques commonly utilised in peptide chemistry.

The compound of the formula II or IIA may be prepared in a preliminary step including a cyclisation step in the presence of a catalyst using as the starting material an aniline compound having a leaving group substituent Y³ at the carbon atom ortho to the amine group substituent, and an N-substituent which is a group —CH₂CH=CHY⁴, in which the aniline derivative is reacted under cyclisation conditions, to form a dihydropyrrole or di- or tetrahydroquinoline ring.

The starting compound for such a cyclisation reaction may be represented by the general formula IV

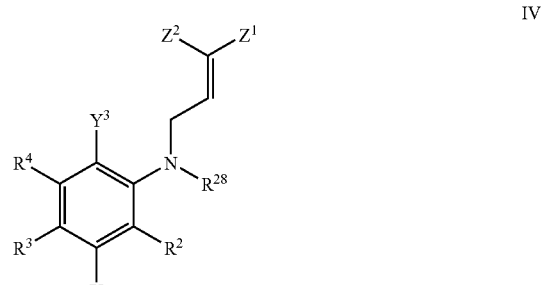
IV in which R², R³, R⁴, X⁴ and Y¹ are the same as in the compound of the formula II;

$R^{28}$ is an amine protecting group,
one of $Z^1$ and $Z^2$ is $Y^4$ and the other is H;
$Y^4$ is H, or is a leaving group which is different from or the same as $Y^1$; and
$Y^3$ is a radical leaving group.
$Y^3$ is preferably a halogen atom, more preferably Br or I.

When cyclisation to form a dihydropyrrole ring is desired, the group $Z^1$ is $Y^4$, and $Y^4$ is either H or a leaving group, preferably the same group as $Y^1$. (In this reaction $Y^4$ is not active as a leaving group but may be so in subsequent steps of the synthesis.) The reaction is conducted in the presence of a suitable catalyst, optionally in the presence of a free radical trap. A group $Y^4$ is preferably I. Where $Y^4$ is a leaving group the cyclisation may be carried out in the presence of radical derived from azoisobutyronitrile. Suitable catalysts for such a radical cyclisation step are tin hydride compounds such as tributyl tin hydride. Such a synthetic route is illustrated in Example 1.

Suitable radicals for carrying out the cyclisation reaction using a compound IV in which $Y^4$ is H are nitroxy compounds such as 2,2,6,6-tetramethylpiperidinyloxy (TEMPO) radical.

For cyclisation to form a six-membered ring it is preferred to use a compound IV in which $Z^2$ is $Y^4$ and $Y^4$ is a leaving group, preferably a trialkyl stannyl group, and to carry out the reaction in the presence of a suitable catalyst palladium complexes such as tetrakis (triphenylphosphine) palladium (0), bis(triphenyl phosphine) palladium (II) chloride or palladium (II) acetate. In this reaction $Y^4$ is active as a leaving group. The dihydroquinoline intermediate is oxidised to form a further intermediate which is an epoxide, for instance using a peroxide reagent. The epoxide intermediate is reduced using a suitable selective reducing agent such as a dialkyl aluminium hydride to produce the corresponding tetrahydroquinoline alcohol which is subsequently halogenated, for instance using carbon tetrachloride/triphenyl phosphine. This reaction is illustrated in Example 2.

The compound of the general formula IV may be produced by alkylation of the sodium salt of the corresponding amiline derivative with a trans-1,3-dihaloprop-2-ene compound.

The carboxylic acid derivative of the general formula III may be synthesised using the methods generally described in Boger et al, 1997 op.cit., for instance PDE-I and PDE-II may be synthesised using the Umezawa synthesis, the Rees-Moody synthesis, the Magnus synthesis, the Cava-Rawal synthesis, the Boger-Coleman synthesis, the Sundberg synthesis, the Martin synthesis, the Tojo synthesis. Indole-2-carboxylic acid is commercially available. Other analogues of the DNA binding sub-units of the duocarmycins, and reactive carboxylic acid derivatives thereof are described by Boger et al, op.cit. and in U.S. Pat. No. 5,843,937.

The present invention relates to the creation of a range of prodrugs that have little or no cytotoxic effects when in their normal state, but are highly cytotoxic (i.e. have a substantially increased cytotoxicity) when activated by oxidation or hydroxylation by CYP enzymes. This provides for a self-targeting drug delivery system in which a non cytotoxic (or negligibly cytotoxic) compound can be administered to a patient, for example in a systemic manner, the compound then being activated at the site of the tumour cells (intratumoural activation) to form a highly cytotoxic compound which acts to kill the tumour cells. The fact that the CYP isoforms are not expressed by normal cells mean that the activation of the compound only occurs at the site of the tumour cells and therefore only tumour cells are affected, thus providing a self-targeting system.

The prodrugs of the present invention have the distinct advantage of being useful in the treatment of tumours at any site in the body, meaning that even tumours that have undergone metastasis (which are normally not susceptible to site specific therapies) may be treated.

The prodrug may be an antitumour prodrug. Examples of tumours include cancers (malignant neoplasms) as well as other neoplasms e.g. innocent tumours. The prodrug may be activated by hydroxylation by isoforms of cytochrome P450's. In a variation of the normal procedure which relies upon CYP expression within tumour cells to effect selective hydroxylation and hence activation of the prodrugs, the selectivity between tumour tissue and normal tissue can be enhanced in a two part procedure.

Thus (a) infecting tumor cells with a viral vector carrying a cytochrome P450 gene and a cytochrome P450 reductase gene, wherein expression of cytochrome P450 gene and cytochrome P450 reductase gene by tumor cells enables the enzymatic conversion of a chemotherapeutic agent to its cytotoxic form within the tumor, whereby the tumor cells become selectively sensitized to the prodrug chemotherapeutic agent (b) contacting tumor cells with the prodrug chemotherapeutic agent whereby tumor cells are selectively killed.

Thus the intratumoural hydroxylation of the prodrugs of the present invention provides them with a surprising and unexpected efficacy.

Hydroxylated forms of the prodrugs are potent DNA alkylating agents that bind in the minor groove of DNA and alkylate the purine bases at the N3 position. As such, they are potent cytotoxic agents whose exact biological mechanism of action is unknown but involves the disruption of template and other functions of DNA. General inhibition of template function of DNA will affect and be generally cytotoxic to all dividing cells in the body and lead to unacceptable side effects in a therapeutic setting. However, the targetted production of hydroxylated forms only in tumour cells that overexpress particular isoforms of cytochrome P450's will lead to a specific cytotoxic effect only in those cells. The non-hydroxylated forms are essentially non-toxic to all cells.

The following examples illustrate the invention.

EXAMPLE 1

The synthesis of one compound of the general formula I is carried out according to the following reaction scheme.

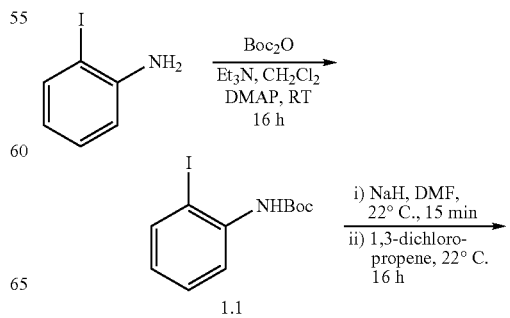

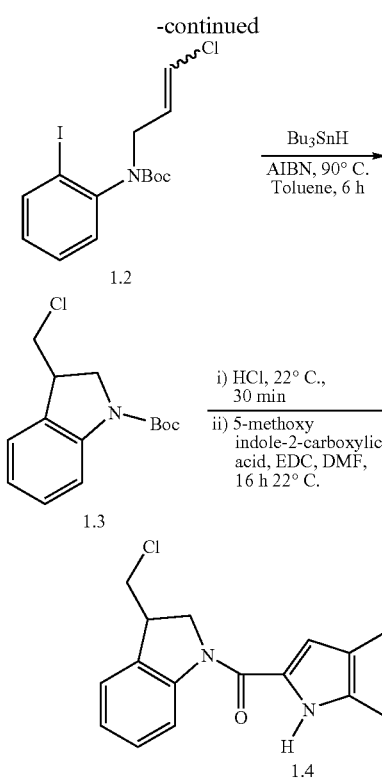

1.1 1-((tert-Butyloxy)carbonyl)amino-2-iodobenzene

A mixture of 2-iodoaniline (100 mg, 0.46 mmol), dichloromethane (DCM) (4 ml), di-tertiary butyl dicarbonate (BOC-dicarbonate) (119 mg, 0.55 mmol), Et₃N (76 μl, 0.55 mmol) and catalytic (dimethylamino) pyride (DMAP) (2 mg) was stirred for 20 hrs. The reaction was concentrated and purified by flash chromatography 4-(DCM/Hex are 1:1) to afford the product (50 mg, 34%) as a off white powdery solid.

1.2 1-N-(Chloro-2-propen-1-yl)-N-((tert-butyloxy)carbonyl)amino-2-iodobenzene A stirred solution of 1-((tert-butyloxy)carbonyl)amino-2-iodobenzene (100 mg, 0.31 mmol) in DMP (dimethyl formamide) (2 ml) was cooled to 0° C. and treated with sodium hydride (NaH) (41 mg, 1.0 mmol). After 15 min, 1,3-dichloropropene (95 μl, 1.01 mmol) was added. The mixture was allowed to warm to 25° C. and stirred for 20 hrs. It was concentrated, H₂O (10 ml) was added and the aqueous layer was extracted with EtOAc (3×10 ml). The combined organic layers were dried (MgSO₄) and concentrated. The residue was purified by flash chromatography (Silica gel, 1 to 10% EtOAc/Hexanes gradient) to furnish the title compound (46 m, 37%) as a yellow oil.

1.3 3-Chloromethyl-2,2-dihydro-1-((tert-butyloxy)carbonyl)indole

A stirred mixture of 1-N-(3-Chloro-2-propen-1-yl)-N-((tert-butyloxy)carbonyl)amino-2-iodobenzene (200 mg, 0.51 mmol), (Bu₃Sn)₂O (38 μL, 0.076 mmol), poly(methylhydrosiloxane) (PMHS) (1439 μL, 0.019 mmol), azoisobutyro nitrile (AIBN) (8.34 mg, 0.051 mmol) in toluene (4 mL) was heated under N₂ for 3 h at 80° C. The reaction was cooled and quenched with EtOAc (20 ml). The solution was washed with water (2×20 ml), dried (MgSO₄) and concentrated. The residue was purified by chromatography (Silica, 1 to 10% EtOAc/Hexanes) to afford the title compound (159 mg, 85.5%) as a clear oil.

1.4 5-Methoxyindole extended agent. 1-chloromethyl-6-benzoyl-3-((5-methoxy-1H-indol-2-yl)carbonyl)-1,2dihydro-3H-pyrrolo[3,2-e]indole 3-Chloromethyl-2,2-dihydro-1-((tert-butyloxy)carbonyl) indole (100 mg, 0.37 mmol) is treated with a solution of hydrochloric acid in ethyl acetate (4M, 500 μL). After 30 min, the solvent is concentrated and DMF (1 mL) is added. The solution was treated with 1-[(3-dimethylamino)propyl]-3-ethylcarbodimide (EDC) (140 mg, 0.73 mmol) and 5-methoxyindole-2-carboxylic acid (140 mg, 0.73 mmol). After 16 h, the solvent was removed under reduced pressure. Chromatography (Silica gel, 2×15 cm, 10% ethyl acetate/hexanes) gave the product.

EXAMPLE 2

The following example illustrates the synthesis of a precursor of a compound of the general formula IA. The product is suitable for extending by a step analogous to step 1.4 to form a compound of the formula IA.

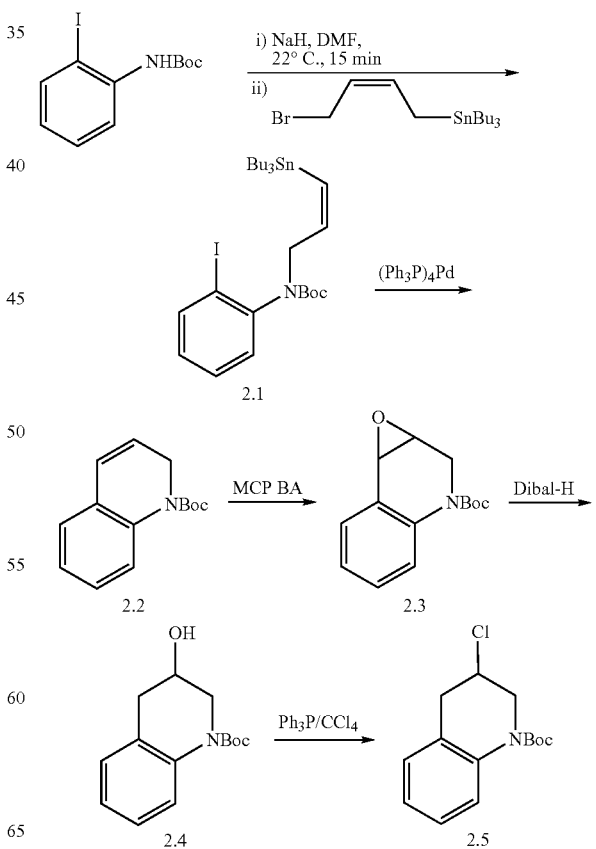

2.1 1-N-(3-(tributylstannyl)-2-propen-1-yl)-N-((tert-butyloxy)carbonyl) amino-2-iodobenzene 1-((tert-butyloxy)carbonyl)amino-2-iodobenzene (synthesised as set out in example 1.1) (100 mg, 0.32 mmol) was stirred in DMF (5 mL) and sodium hydride (38 mg, 0.96 mmol, 60% dispersion in oil, 3 equiv.) was added. After 15 min, the suspension was treated with E/Z-1-tributylstannyl-3-bromopropene (392 mg, 0.92 mmol, 3 equiv) and the resulting solution was stirred at RT for 16 h. The solution was concentrated and water (10 mL) was added. The aqueous solution was extracted with ethyl acetate (3×10 mL), the organic layers combined, dried and concentrated. The product (145 mg, 70%) was obtained after chromatography (Silica gel, 2×15 cm, 10% ethyl acetate/hexanes). FABMS (NBA/NaI) 649 (M+H$^+$ expected 649).

2.2 1-((tert-butyloxy)carbonyl)-1,2-dihydroquinoline

1-N-(3-(tributylstannyl)-2-propen-1-yl)-N-((tert-butyloxy)carbonyl)amino-2-iodobenzene (100 mg, 0.15 mmol) and tetrakis(triphenylphosphine) palladium(0) (32 mg, 0.2 equiv) were stirred in toluene (2 mL) at 50° C. under N$_2$ for 12 h. The solvent was then removed in vacuo. Chromatography (SiO$_2$, 10% ethyl acetate/hexanes) gave the product (35 mg, 100%) as a yellow oil. FABMS (NBA/NaI) 232 (M+H$^+$ expected 232).

2.3 1-((tert-Butyloxy)carbonyl)-3,4-epoxy-1,2,3,4-tetrahydroquinoline 1-((tert-Butyloxy)carbonyl)-1,2-dihydroquinoline (100 mg, 0.43 mmol) and MCPBA (109 mg, 0.65 mmol, 1.5 equiv) were stirred in CH$_2$Cl$_2$ (2 mL) at −78° C. to −30° C. under N$_2$ for 2 h. The solvent was then removed in vacuo. Chromatography (SiO$_2$, 10% ethyl acetate/hexanes) gave the product (100 mg, 94%) as a colourless oil. FABMS (NBA/NaI) 248 (M+H$^+$ expected 248).

2.4 1-((tert-Butyloxy)carbonyl)-4-hydroxy-1,2,3,4-tetrahydroquinoline 3,4-epoxy-1-((tert-butyloxy)carbonyl)-1,2,3,4-tetrahydro-5,6-benzoquinoline (100 mg, 0.41 mmol) was treated with Dibal-H (91 mg, 0.62 mmol, 1.5 equiv) in THF (2 mL) at −78 ° C. under N$_2$. After 1 h, the reaction was quenched by the addition of water (2 mL) and the resulting solution was extracted with ethyl acetate (3×10 mL), the organic layers combined, dried and concentrated. Chromatography (SiO2, 10% ethyl acetate/hexanes) gave the alcohol (75 mg, 63%) as a colourless solid. FABMS (NBA/NaI) 250 (M+H$^+$ expected 250).

2.5 1-((tert-Butyloxy)carbonyl)-4-chloro-1,2,3,4-tetrahydroquinoline 1-((tert-Butyloxy)carbonyl)-4-hydroxy-1,2,3,4-tetrahydroquinoline.(100 mg, 0.40 mmol) in CH$_2$Cl$_2$ (2 mL)was treated with a prepared solution of PPh$_3$ (212 mg, 0.80 mmol, 2 equiv) and CCl$_4$ (500 μL) in CH$_2$Cl$_2$ (2 mL) at RT. After 16 h, the solvent was removed in vacuo. Chromatography (SiO$_2$, 10% ethyl acetate in hexanes) gave the chloride (65 mg, 61%) FABMS (NBA/NaI) 268 (M +H$^+$ expected 268). The compound could be conjugated to a DNA binding subunit after deprotection by a method analogous to the steps of EXAMPLE 3.4 below.

EXAMPLE 3

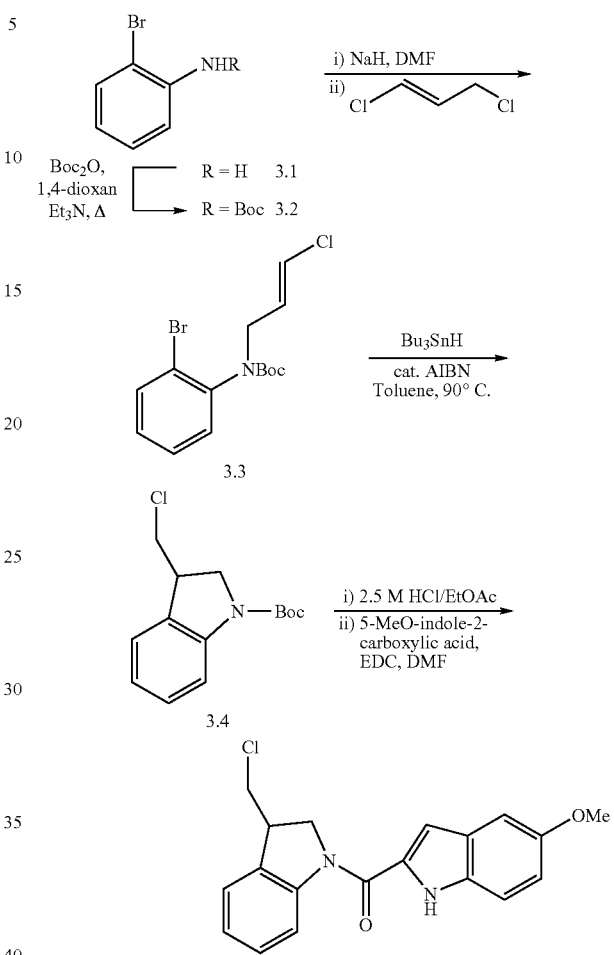

3.1 2-bromo-N-(tert-Butoxy carbonyl) aniline (3.2)

A solution of 2-bromoaniline (100 mg, 0.58 mmol), Boc-dicarbonate (507 mg, 2.32 mmol) and Et$_3$N (81 μl, 0.58 mmol) in 1,4-dioxan (10 ml) was heated to 100° C. under N$_2$ for 48 h. Upon completion, the resulting mixture was cooled, concentrated and purified by chromatography (SiO$_2$, EtOAc/Hex 1:9) to afford 2 (116 mg, 73%) as a clear film. $^1$H NMR (CDCl$_3$, 500 MHz) FABMS (NBA/NaI): 271 (M+H$^+$ expected 271), 295 (M+Na$^+$ expected 295).

3.2 2-Bromo-N-(tert-butyloxycarbonyl)-N-(3-chloro-2-propen-1-yl) aniline (3.3)

A solution of 3.2 (350 mg, 1.29 mmol) in DMF (7 ml) was cooled to 0° C. and NaH (93 mg, 3.85 mmol) was added. The resulting mixture was stirred for 15 mins and 1,3 dichloropropene (358 μl, 3.85 mmol) was added. The mixture was allowed to warm to 25 ° C. and stirred for 15 h. The mixture was then concentrated. H$_2$O (10 ml) was added to the residue and the solution was extracted with EtOAc (3×10 ml). The combined organic layers were dried with MgSO$_4$ and concentrated. The residue was purified by flash chromatography (SiO$_2$, EtOAc/Hex 1:9) to afford 3.3 (400 mg, 89%) as a pale yellow oil. FABMS (NBA/NaI) 346 (M+H$^+$ expected 346).

3.3 1-(tert-Butyloxycarbonyl)-3-(chloromethyl) indoline (3.4)

A solution of 3.3 (110 mg, 0.318 mmol) and AIBN (21 mg, 0.127 mmol) in dry toluene (10 ml) was degassed for 15 mins with N$_2$ and then heated to 90° C. Bu$_3$SnH (84 μl, 0.318 mmol) was added to the mixture in four portions over an hour and the resulting mixture was stirred at 90° C. for a further 2 h. The mixture was then concentrated and purified by flash chromatography (SiO$_2$, 0–10% EtOAc in hexane) to afford 3.4 (50 mg, 59%) as a colourless oil.FAB MS: (NBA/NaI) 267, (M+H$^+$, expected 267) 292 (M+Na$^+$, expected 292).

3.4 3-(Chloromethyl)-1--[(5-methoxyindol-2-yl) carbonyl]indoline (3.5)

Compound 3.4 (100 mg, 0.38 mmol) was treated with 2.5 M HCl in EtOAc (1 mL) and the solution was stirred for 30 min. The solvent was removed under a stream of nitrogen and the grey residue was dissolved in DMF (10 mL). 5-Methoxyindole-2-carboxylic acid (215 mg, 1.14 mmol) and EDC (215 mg, 1.14 mmol) were added and the mixture stirred for 16 h. Solvent was removed in vacuo and the residue subjected to flash chromatography (SiO$_2$, EtOAc/ hexanes 1:1) to give the product as a red oil (100 mg, 76%). FABMS (NBA/NaI) 341 (M+H$^+$ expected 341).

EXAMPLE 4

Biological Testing of 3-(Chloromethyl)-1--[(5-methoxyindol-2-yl)carbonyl]indoline Materials and Methods 4.1 Incubation mixtures of test compound and microsomes Test compound activation by CYP enzymes was carried out using NADPH supplemented rat liver microsomes. Incubation mixtures comprised microsomal protein (1 mg/ml), reduced-nicotinamide adenine dinucleotide phosphate (NADPH,10 mM) and phosphate buffer (pH7.4, 100 mM). Test compound (0.01–100 μM final concentration) in DMSO (20 μl) was added to the microsomal incubation mixtures (0.5 ml) and incubated for 60 min at 37C. Control incubates contained test compound and microsomal incubation mixture terminated at 0 time. All incubations were terminated by addition of an equal volume of ice-cold acetonitrile and microfuged for 3 min. Aliquots of the supernatant were added to cells in culture.

4.2 Cell Culture Based Cytotoxicity Measurement

Chinese Hamster Ovary (CHO) cell were grown in MEM supplemented with 10% dialysed FBS and G418 (400 μg/ml). All cells were seeded at an initial density of 1000 cells/well in 96-well-plates, incubation at 37° C. for 24 hours. Aliquots (0.1 ml) of the test compound/microsomal/ acetonitrile supernatnant was then added to the CHO cells. Cells were then incubated for 24 hours at 37° C., 5% CO$_2$. After this time period MTT (50 μl; 2 mg/ml stock solution) was added to each well and cells were incubated for a further 4 hours. During this time period MTT, a hydrogen acceptor tetrazolium salt, is reduced to formazan dye by mitochondrial dehydrogenase of viable cells. The media was aspirated from cells and DMSO (100 μl/well) added to solubilise the is coloured formazan dye. Absorbance of the formazan dye in the 96-well-plates was then determined at 550 nm. The effect of microsomal activation by the test compound on the arrest of CHO cell growth could be determined by comparing the IC$_{50}$ (concentration that inhibited cell growth by 50%) with and without microsomal incubation.

| Results | | | |
|---|---|---|---|
| | CHO IC50 (μM) | | |
| compound | +activation | −activation | AF |
| 3.5 | 0.13 ± 0.03 | 5.51 ± 0.23 | 42.4* |

AF = activity factor i.e. the ratio of IC$_{50}$ cytotoxicity values obtained for ± compound 3.5 activation
*represents significance at p > 0.05.

Effect of compound 3.5 and its metabolism (activation) product on the survival of Chinese hamster ovary cells in culture. Cells were incubated for 24 hours with supernatants from reaction mixtures of compound 3.5 with NADPH fortified rat liver microsomes. IC$_{50}$ represents the concentration of drug required to inhibit cell growth by 50%. Values are expressed as the mean±sd for three experiments. See methods for full details of metabolism.

The invention claimed is:

1. A compound selected from the group consisting of:
   1-(chloromethyl)-6-benzoyl-3-((5-methoxy-1H-indol-2-yl)carbonyl)-1,2dihydro-3H-pyrrolo[3,2-e]indole; and
   3-(chloromethyl)-1-[(5-methoxyindol-2-yl)carbonyl]indoline.

2. A pharmaceutical composition comprising a compound of the general formula I

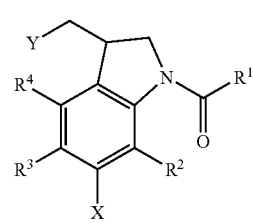

in which X is H;
Y is a leaving group;
R$^1$ is —Ar, NH$_2$, or R$^8$;
R$^2$ and R$^3$ are each independently selected from the group consisting of H, C$_{1-4}$ alkyl, —OH, C$_{1-4}$ alkoxy, —CN, Cl, Br, I, —NO$_2$, —NH$_2$, —NHCOR$^9$, —COOH, CONHR$^{10}$, —NHCOOR$^{10}$ and —COOR$^{10}$;
R$^4$ is selected from the group consisting of H, C$_{1-4}$ alkyl, CN, Cl, Br, I, NO$_2$, NH$_2$, —NHCOR$^9$, —COOH, —CONHR$^{10}$, —NHCOOR$^{10}$ and —COOR$^{10}$;
R$^8$, R$^9$ and R$^{10}$ are independently selected from the group consisting of C$_{1-4}$ alkyl, optionally substituted phenyl, C$_{7-12}$-aralkyl, optionally substituted heteroaryl and ligands;
Ar is selected from the group consisting of

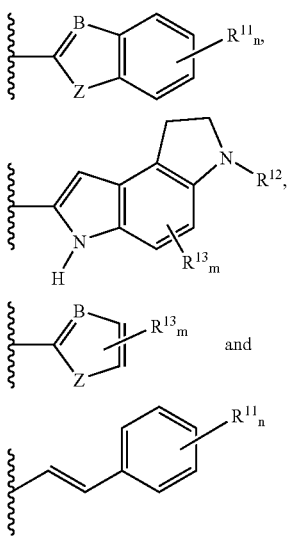

in which B is N or CR$^{14}$;

Z is selected from the group consisting of O, S —CH=CH— and NH;

the or each R$^{11}$ is selected from the group consisting of OH, C$_{1-4}$ alkoxy, C$_{1-4}$ alkyl, —NO$_2$, —NH$_2$, —NHR$^{17}$, —NR$^{17}$$_2$, —N$^+$R$^{17}$$_3$, —CN, Cl, Br, I, —NHCOR$^{15}$, —COOH, —CONHR$^{16}$, —NHCOOR$^{16}$ and —COOR$^{16}$;

n is an integer in the range 0 to 4;

R$^{12}$ is selected from the group consisting of H, —COAr$^1$, —CONH$_2$, —COOH, —COR$^{16}$ and —COOR$^{16}$;

the or each R$^{13}$ is selected from the group consisting of OH, C$_{1-4}$ alkoxy, C$_{1-4}$ alkyl, —NO$_2$, —NH$_2$, —NHR$^{17}$, —NR$^{17}$$_2$, —N$^+$R$^{17}$$_3$, —CN, Cl, Br, I, —NHCOR$^{15}$, —COOH, —CONHR$^{16}$, —NHCOOR$^{16}$ and —COOR$^{16}$;

m is 0, 1 or 2;

R$^{14}$ is selected from the group consisting of OH, C$_{1-4}$ alkoxy, C$_{1-4}$ alkyl, —NO$_2$, —NH$_2$, —CN, Cl, Br, I, —NHCOR$^{15}$, —COOH, —CONHR$^{16}$, —COOR$^{16}$, —NHCOOR$^{16}$ and H;

R$^{15}$ is selected from the group consisting of C$_{1-4}$ alkyl, optionally substituted phenyl, optionally substituted heteroaryl, C$_{7-12}$ aralkyl, a ligand and Ar$^1$;

R$^{16}$ is selected from the group consisting of C$_{1-4}$ alkyl, optionally substituted phenyl, C$_{7-12}$-aralkyl and optionally substituted heteroaryl and a ligand;

each R$^{17}$ is selected from the group consisting of C$_{1-4}$-alkyl, optionally substituted phenyl, optionally substituted heteraryl and C$_{7-12}$-aralkyl; and Ar$^1$ is selected from the same groups as Ar, and provided that no more than one group R$^{11}$ or R$^{13}$ in any one ring includes a group Ar$^1$; and a pharmaceutically acceptable excipient.

3. A compound having the general formula IA

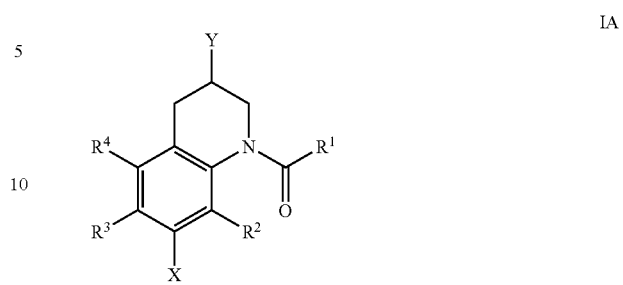

in which X is H;

Y is a leaving group;

R$^1$ is —Ar, NH$_2$, or R$^8$;

R$^2$ and R$^3$ are each independently selected from the group consisting of H, C$_{1-4}$ alkyl, —OH, C$_{1-4}$ alkoxy, —CN, Cl, Br, I, —NO$_2$, —NH$_2$, —NHCOR$^9$, —COOH, CONHR$^{10}$, —NHCOOR$^{10}$ and —COOR$^{10}$;

R$^4$ is selected from the group consisting of H, C$_{1-4}$ alkyl, CN, Cl, Br, I, NO$_2$, NH$_2$, —NHCOR$^9$, —COOH, —CONHR$^{10}$, —NHCOOR$^{10}$ and —COOR$^{10}$;

R$^8$, R$^9$ and R$^{10}$ are independently selected from the group consisting of C$_{1-4}$ alkyl, optionally substituted phenyl, C$_{7-12}$-aralkyl, optionally substituted heteroaryl and ligands;

Ar is selected from the group consisting of

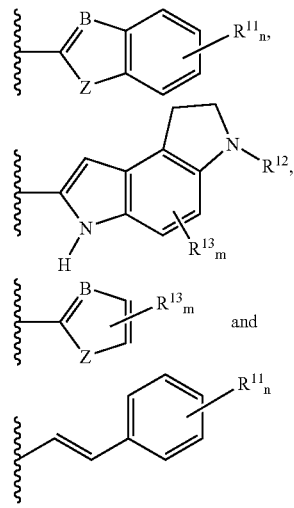

in which B is N or CR$^{14}$;

Z is selected from the group consisting of O, S —CH=CH— and NH;

the or each R$^{11}$ is selected from the group consisting of OH, C$_{1-4}$ alkoxy, C$_{1-4}$ alkyl, —NO$_2$, —NH$_2$, —NHR$^{17}$, —NR$^{17}$$_2$, —N$^+$R$^{17}$$_3$, —CN, Cl, Br, I, —NHCOR$^{15}$, —COOH, —CONHR$^{16}$, —NHCOOR$^{16}$ and —COOR$^{16}$;

n is an integer in the range 0 to 4;

R$^{12}$ is selected from the group consisting of H, —COAr$^1$, —CONH$_2$, —COOH, —COR$^{16}$ and —COOR$^{16}$;

the or each R$^{13}$ is selected from the group consisting of OH, C$_{1-4}$ alkoxy, C$_{1-4}$ alkyl, —NO$_2$, —NH$_2$, —NHR$^{17}$, —$NR^{17}{}_2$, —$N^+R^{17}{}_3$, —CN, Cl, Br, I, —$NHCOR^{15}$, —COOH, —$CONHR^{16}$, —$NHCOOR^{16}$ and —$COOR^{16}$;

m is 0, 1 or 2;

$R^{14}$ is selected from the group consisting of OH, $C_{1-4}$ alkoxy, $C_{1-4}$ alkyl, —$NO_2$, —$NH_2$, —CN, Cl, Br, I, —$NHCOR^{15}$, —COOH, —$CONHR^{16}$, —$COOR^{16}$, —$NHCOOR^{16}$ and H;

$R^{15}$ is selected from the group consisting of $C_{1-4}$ alkyl, optionally substituted phenyl, optionally substituted heteroaryl, $C_{7-12}$ aralkyl, a ligand and $Ar^1$;

$R^{16}$ is selected from the group consisting of $C_{1-4}$ alkyl, optionally substituted phenyl, $C_{7-12}$-aralkyl and optionally substituted heteroaryl and a ligand;

each $R^{17}$ is selected from the group consisting of $C_{1-4}$-alkyl, optionally substituted phenyl, optionally substituted heteraryl and $C_{7-12}$-aralkyl; and $Ar^1$ is selected from the same groups as Ar, and provided that no more than one group $R^{11}$ or $R^{13}$ in any one ring includes a group $Ar^1$.

4. A compound according to claim 3 which is 1-((5-methoxy-1H-indol-2-yl)carbonyl)-4-chloro-1,2,3,4-tetrahydroquinoline.

5. A pharmaceutical composition comprising a compound according to claim 3 and a pharmaceutically acceptable excipient.

6. A compound according to claim 3 in which $R^1$ is Ar; and

Ar is a group

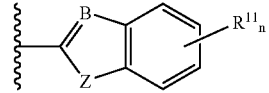

7. A compound according to claim 6 in which n is 0;

B is $CR^{14}$;

z is NH; and $R^{14}$ is H.

8. A compound according to claim 6 in which

Y is Cl.

* * * * *